US00PP25970P3

(12) United States Plant Patent
Olesen

(10) Patent No.: US PP25,970 P3
(45) Date of Patent: Oct. 6, 2015

(54) MINIATURE ROSE PLANT NAMED 'POULPAH068'

(50) Latin Name: ***Rosa* hybrid**
Varietal Denomination: Poulpah068

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 48 days.

(21) Appl. No.: 13/986,932

(22) Filed: Jun. 14, 2013

(65) Prior Publication Data

US 2014/0373204 P1 Dec. 18, 2014

(51) Int. Cl.
*A01H 5/02* (2006.01)

(52) U.S. Cl.
USPC ..... Plt./116

(58) Field of Classification Search
USPC ..... Plt./116, 123, 141
CPC ..... A01H 5/0222; A01H 5/0216; A01H 5/02; A01H 5/00
See application file for complete search history.

(56) References Cited

PUBLICATIONS

Poulsen Roser A/S. Vina Hit, retrieved on Jan. 12, 2015, retrieved from the Internet at <www.poulsenroser.com/assortment/rose-collections/patiohit/vina-hit.aspx> one page.*
Upov Pluto Plant Variety Database 20150114 retrieved on Jan. 14, 2015, retrieved from the Internet <www3.wipo.int/pluto/user/en/index.jsp> for Rosa 'Poulpah068' one page.*

* cited by examiner

*Primary Examiner* — June Hwu

(57) ABSTRACT

A new miniature rose plant that has abundant pink with white striping flowers and attractive foliage. The variety successfully propagates from softwood cuttings and is suitable for year-round production in commercial glasshouses. This new and distinct variety has shown to be uniform and stable in the resulting generations from asexual propagation.

2 Drawing Sheets

Botanical designation: *Rosa* hybrid.
Variety denomination: 'Poulpah068'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulpah068', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant flowers that are pink with white stripes;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpah068' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpah068' was selected by the inventor as a single plant from the progeny of the hybridization in 2007.

Asexual reproduction of 'Poulpah068' by vegetative stem cuttings was first done by Mogens N. Olesen in the nursery in Fredensborg, Denmark in 2008. This initial and other subsequent propagations conducted in controlled environments have demonstrated that the characteristics of 'Poulpah068' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah068'.

Specifically illustrated in FIG. 1 are flowers at various stages of development, flower in parts, mature leaves, and stems.

DETAILED DESCRIPTION OF THE VARIETY

Figure 1:
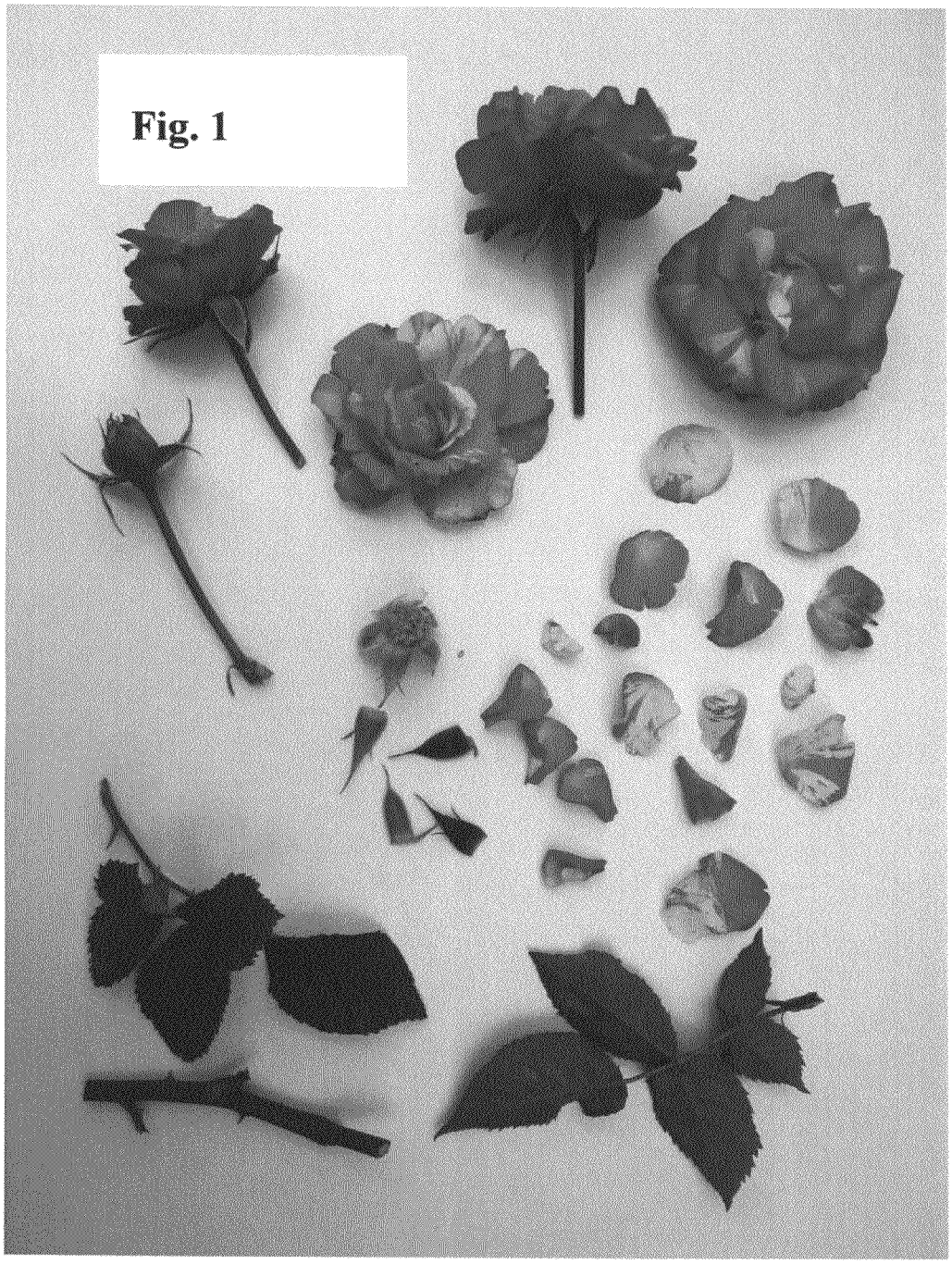
Figure 2:
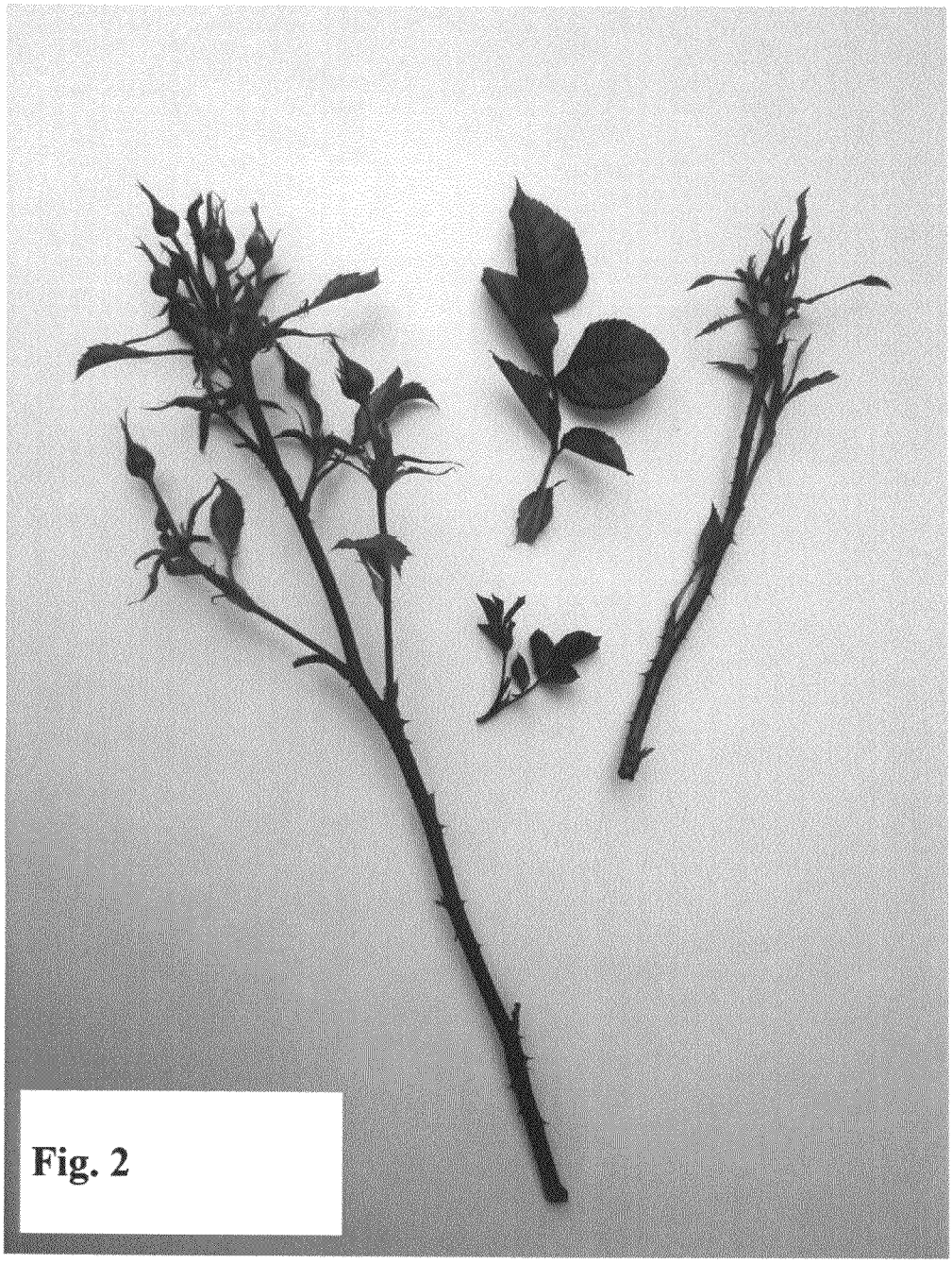
FIG. 2 demonstrates juvenile leaves, stems, and flower buds.

The following is a description of 'Poulpah068', as observed in its growth in a field nursery in Benton County Oreg. Observed plants are 10 months of age and were cultivated on their own roots. Color references are made using The Royal Horticultural Society (London, England) Colour Chart, 2001, except where common terms of color are used.

For a comparison, several physical characteristics of the rose variety 'Poulpah024', U.S. Plant Pat. No. 18,729 are compared to 'Poulpah068' in Chart 1.

CHART 1

| | 'Poulpah068' | 'Poulpah024' |
|---|---|---|
| Petalage: | 20 | 90 petals, 10 to 15 of which are petaloids |
| Flower Diameter: | 75 mm | 55 to 60 mm |
| General Tonality of Flower Color: | Red Group 52A with intonations of Red Group 43D. Splashed with White Group N155B. | Red-Purple Group 57A with streaks of White Group 155A and Yellow Group 5D |

FLOWER AND FLOWER BUD

Blooming habit: Continuous.

Flower bud:

*Size*.—Upon opening, 20 mm in length from base of receptacle to end of bud. 10 mm in diameter.

*Bud form*.—Urceolate.

*Bud color*.—As sepals unfold, petals are petals are Orange-Red Group N34A and Red Group 41B. Additional intonations of Orange Group 29A and Green-White Group 157A.

*Sepals*.—Upper Surface: Color: Yellow-Green Group 144C with strong intonations of Greyed-Red Group 181B. Texture: Smooth, moderately pubescent. Lower Surface: Color: Yellow Green Group 144A with intonations of Greyed-Purple Group 183A. Texture: Rough with stipitate glands. Shape: Apex: Cirrhose. Base: Flat at union with receptacle. Margins: Margins have moderate foliaceous appendages on three of the five sepals. Size: 26 mm long by 8 mm wide.

*Receptacle*.—Surface Texture: Smooth. Shape: Funnel shaped. Size: 5 mm tall and 7 mm wide. Color: Greyed-Purple Group 183A and Yellow Green Group 144A.

*Pedicel*.—Surface: Smooth with few stipitate glands. Length: 30 to 55 mm. Diameter: Generally 3 mm. Color: Greyed-Red Group 178A and Yellow-Green Group 144A. Strength: Medium strength.

*Peduncles*.—Length: 10 to 70 mm. Diameter: 3 mm on average. Color: Yellow-Green Group 144A with Greyed-Red Group 178A. Surface: Smooth.

Flower bloom:

*Borne*.—In clusters from 3 to 7 flowers on each flowering branch.

*Fragrance*.—Light floral scent.

*Duration*.—As a pot plant, flowers last up to 21 days.

*Size*.—Flower diameter is about 75 mm when open. Flower depth is 25 mm.

*Form*.—Semi-double. General shape is a hybrid tea with a high pointed center.

Petalage: Under normal conditions, flowers have about 20 petals total, 2 to 3 of which are petaloids.

Color:

*General tonality*.—On open flowers are Red Group 52A with intonations of Red Group 43D. Splashed with White Group N155B.

*Upon opening*.—Outer and inner petals are Red Group 52A and 52C splashed with White Group N155B on the upper surface. The base of the upper surface is a petal spot Yellow Group 4D. Red Group 52A splashed with White Group N155C on the lower surface. On the lower surface at the base of the petal is Yellow-Green Group 4D.

*After opening, petals*.—Outermost and innermost petals are Red Group 52B and 52C, splashed with White Group N155B on the upper surface. The lower surface is Red Group 52A and 52C, splashed with White Group N155C.

Petals:

*Petal reflex*.—Moderate to strong.

*Margin*.—Entire. Strong undulations. Multiple clefts at the margin.

*Shape*.—Generally broad and elliptic. Apex shape: Rounded. Base shape: Rounded.

*Size*.—35 mm (l) by 45 mm (w).

*Texture*.—Smooth.

*Thickness*.—Average.

Reproductive organs:

*Pollen*.—None Observed.

*Anthers*.—Size: 2 mm long. Color: Yellow Group 4C with Greyed-Orange Group 163B. Quantity: 55 on average.

*Filaments*.—Color: Yellow Group 8A. Length: About 3 mm.

*Pistils*.—Length: About 3 mm long. Quantity: 15 on average.

*Stigmas*.—Even relative to the length of the filaments and the height of the anthers. Color: Greyed-Yellow Group 162C.

*Styles*.—Color: Green-White Group 157A and Red Group 43B.

*Seed formation*.—Not observed.

PLANT

Plant growth: Upright. Plants are 40 cm in height, and 35 cm wide.

Stems:

*Color*.—Juvenile growth: Yellow-Green Group 146C with strong anthocyanin the color of Greyed-Purple Group 183B. Mature growth: Yellow-Green Group 146C.

*Length*.—Canes are about 30 cm from the base of the plant to the flowering portion.

*Diameter*.—8 mm.

*Internodes*.—On mature canes, there is an average distance of 45 mm between nodes.

*Surface texture*.—Young and mature wood is rough with various sizes of prickles.

Long prickles:

*Incidence*.—5 per 10 cm of stem.

*Size*.—Average length: 4 mm.

*Color*.—Juvenile prickles are Greyed-Purple Group 184B. Mature prickles are Greyed-Purple Group 184B.

*Shape*.—Above linear, below concave.

Plant foliage:

*Compound leaf size*.—120 mm (l) by 85 mm (w).

*Quantity.*—2 leaves per 10 cm of stem.

*Color of juvenile foliage.*—Upper Leaf Surface: Greyed-Purple Group 183A. Lower Leaf Surface: Greyed-Purple Group 183A.

*Color of mature foliage.*—Upper Leaf Surface: Yellow-Green Group 146A to 147A. Lower Leaf Surface: Yellow-Green Group 146B.

Plant leaves and leaflets:

*Stipules.*—Size: About 12 mm in length. Shape: Linear, slightly broad based with outward extending apecies. Margins: Finely serrated with few stipitate glands. Color: Yellow-Green Group 144A.

*Petiole.*—Length: 30 mm on average. Diameter: About 2 mm. Upper surface: Yellow-Green Group 144A. Lower surface: Yellow-Green Group 144A with Greyed-Red Group 183C.

*Rachis.*—Length: 35 mm on average. Diameter: About 2 mm. Upper surface: Yellow-Green Group 144A. Lower surface: Yellow-Green Group 144A with Greyed-Red Group 183C with small prickles.

*Leaflet.*—Number of leaflets: 5 on normal leaves in middle of the stem. Size: 50 mm in length by 32 mm wide. Margin: Serrate. General Shape: Elliptical. Apex Shape: Acute. Base Shape: Round. Texture: Smooth. Arrangement: Odd pinnate. Venation: Reticulate. Leaf Gloss: Moderately glossy.

Cold hardiness: The variety is tolerant to USDA Cold Hardiness Zone 6.

Heat tolerance: The variety has been found to be suitable for climate conditions found in the American Horticulture Society heat zone 7.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

The invention claimed is:

1. A new and distinct variety of rose plant of the miniature class named 'Poulpah068', substantially as illustrated and described herein, due to its abundant, pink with white striping flowers, vigorous growth, compact habit, suitability for production from softwood cuttings in pots, and durable flowers and foliage that make the variety suitable for distribution in the floral industry.

* * * * *